(12) United States Patent
Kato et al.

(10) Patent No.: US 9,387,137 B2
(45) Date of Patent: Jul. 12, 2016

(54) ABSORBENT ARTICLE PACKAGE AND METHOD OF FOLDING THE SAME ALONG FOLDING LINES TOWARD OPPOSITE SIDES THEREOF

(75) Inventors: Nobuyuki Kato, Kagawa (JP);
Masahiro Kashiwagi, Kagawa (JP);
Tatsuya Tamura, Kagawa (JP);
Masashi Kitagawa, Kagawa (JP)

(73) Assignee: Unicharm Corporation, Ehime (JP)

( * ) Notice: Subject to any disclaimer, the term of this patent is extended or adjusted under 35 U.S.C. 154(b) by 391 days.

(21) Appl. No.: 13/976,233

(22) PCT Filed: Dec. 27, 2011

(86) PCT No.: PCT/JP2011/080222
§ 371 (c)(1),
(2), (4) Date: Aug. 7, 2013

(87) PCT Pub. No.: WO2012/091016
PCT Pub. Date: Jul. 5, 2012

(65) Prior Publication Data
US 2013/0317470 A1 Nov. 28, 2013

(30) Foreign Application Priority Data
Dec. 27, 2010 (JP) .................. 2010-290079

(51) Int. Cl.
*A61F 13/15* (2006.01)
*A61F 13/20* (2006.01)
*A61F 13/551* (2006.01)

(52) U.S. Cl.
CPC ....... *A61F 13/5514* (2013.01); *A61F 13/15577* (2013.01); *A61F 13/15747* (2013.01)

(58) Field of Classification Search
CPC ............. A61F 2013/49033; A61F 2013/49036
USPC ...................................... 604/385.02
See application file for complete search history.

(56) References Cited

U.S. PATENT DOCUMENTS 5,569,228 A * 10/1996 Byrd .................. A61F 13/5514
206/438
6,616,643 B1 * 9/2003 Costa ................ A61F 13/15747
604/385.02

(Continued)

FOREIGN PATENT DOCUMENTS

| EP | 1 03 004 A2 | 10/2000 |
|---|---|---|
| JP | 10-290819 | 11/1998 |

(Continued)

OTHER PUBLICATIONS

International Search Report from corresponding PCT application No. PCT/JP2011-080222 dated Feb. 14, 2012 (4 pgs).

(Continued)

*Primary Examiner* — Michele M Kidwell
(74) *Attorney, Agent, or Firm* — Brinks Gilson & Lione

(57) ABSTRACT

An absorbent article package is individually packaged by folding a packaging sheet and an absorbent article in a state where the absorbent article is arranged on the packaging sheet. In a state where the individually-packaged absorbent article is opened, in the packaging sheet and the absorbent article, a first folding line based on which the absorbent article and the packaging sheet are folded towards the topsheet side, and a second folding line based on which the absorbent article and the packaging sheet are folded towards the backsheet side are formed adjacent to each other in the longitudinal direction.

10 Claims, 12 Drawing Sheets

(56) References Cited

U.S. PATENT DOCUMENTS

2007/0250031 A1   10/2007   Woltman et al.
2010/0325418 A1*  12/2010   Kanekar ............ H04L 63/0823
                                                             713/151

FOREIGN PATENT DOCUMENTS

| JP | 11-0569010 | 3/1999 |
| JP | 3587616 B2 | 8/2004 |
| JP | 2006-340978 | 12/2006 |
| JP | 2009-005944 | 1/2009 |
| JP | 2009-034276 | 2/2009 |

OTHER PUBLICATIONS

Japanese Office Action and English translation from corresponding Japanese Application No. 2010-290079 dated Oct. 28, 2014 94 pgs).
European extended Search Report from corresponding European application No. 11853836.2 dated May 4, 2015 (8 pgs).

* cited by examiner

ABSORBENT ARTICLE PACKAGE AND METHOD OF FOLDING THE SAME ALONG FOLDING LINES TOWARD OPPOSITE SIDES THEREOF

RELATED APPLICATION

This application is a 35 U.S.C. §371 national phase filing of International Patent Application No. PCT/JP2008/080222, filed Dec. 27, 2011, through which and to which priority is claimed under 35 U.S.C. §119 to Japanese Patent Application No. 2010-290079, filed Dec. 27, 2010.

TECHNICAL FIELD

The present invention relates to an absorbent article package and a method of folding the absorbent article package.

BACKGROUND ART

Conventionally, there has been provided an absorbent article package which is folded multiple times to reduce its size. For example, Patent Literature 1 describes an absorbent article package in which an absorbent article, which includes a liquid-permeable topsheet, a liquid-impermeable backsheet, and an absorber arranged between the topsheet and the backsheet, is packaged individually by being folded multiple times in a state where the absorbent article is arranged on a sheet-like packaging sheet.

A method of folding the absorbent article package includes: a step of arranging the absorbent article on the packaging sheet so that the backsheet of the absorbent article and the packaging sheet face to each other; a step of folding back both ends in the widthwise direction of the absorbent article towards the topsheet side based on two longitudinal folding lines along the longitudinal direction of the absorbent article; and a step of folding back both ends in the longitudinal direction of the absorbent article towards the topsheet side based on two widthwise folding lines along the widthwise direction of the absorbent article.

CITATION LIST

Patent Literature

[PTL 1]
Japanese Patent No. 3587616

SUMMARY OF INVENTION

Herein, at the time of installation of the absorbent article on underwear, the back surface of the absorbent article provided with an adhesive is bonded along the inner surface of the underwear to install the absorbent article on the underwear. At this time, in a case where the absorbent article has been folded back towards one surface side (the topsheet side or the backsheet side), it sometimes happens that the absorbent article cannot be appropriately arranged along the inner surface of the underwear. For example, the absorbent article described in Patent Literature 1 is folded based on the longitudinal folding lines prior to being folded based on the widthwise folding lines, so that the whole of longitudinal folding lines is folded back towards the topsheet side. Therefore, the whole of both ends in the widthwise direction of the absorbent article is folded back towards the topsheet side (the body side) based on the longitudinal folding lines, thereby making it difficult to arrange the both ends in the widthwise direction of the absorbent article along the underwear.

Especially in an absorbent article having wing units, it is necessary to fold back the wing units towards the back surface side to install them on the outer surface of underwear. However, in a case where the longitudinal folding lines folded back towards the topsheet side are formed in the wing units, it is sometimes difficult to install the wing units appropriately on the outer surface of the underwear. Furthermore, in a case where the whole of the longitudinal folding lines of the absorbent article having the wing units is folded back towards the backsheet side, there is a possibility that adhesives provided to the back surfaces of the wing units and an adhesive of the backsheet are bonded together.

Therefore, the present invention has been achieved in view of the aforementioned problem, and an object thereof is to provide an absorbent article which a wearer can install on their underwear easily, and a method of folding the absorbent article.

To solve the problem, an absorbent article package as an exemplified aspect according to the present invention includes an absorbent article including an absorbent main body having a liquid-permeable topsheet, a liquid-impermeable backsheet and an absorber arranged between the topsheet and the backsheet; and a packaging sheet in which the absorbent article is individually packaged, wherein the absorbent article is individually packaged by folding the packaging sheet and the absorbent article in a state where the absorbent article is arranged on the packaging sheet; a folding line in a longitudinal direction of the absorbent article is formed in the packaging sheet and the absorbent article in a state where the individually-packaged absorbent article is opened; and the folding line includes: a first folding line based on which the absorbent article and the packaging sheet are folded towards the topsheet side; and a second folding line adjacent to the first folding line, based on which the absorbent article and the packaging sheet are folded towards the backsheet side.

Furthermore, a method of folding an absorbent article package as another exemplified aspect according to the present invention has: an absorbent article including an absorbent main body having a liquid-permeable topsheet, a liquid-impermeable backsheet, and an absorber arranged between the topsheet and the backsheet; and a packaging sheet in which the absorbent article is individually packaged, and the method includes: a first step of arranging the absorbent article on the packaging sheet; a second step of folding a longitudinal end region of the absorbent article, including each of both ends in the longitudinal direction of the absorbent article, and the packaging sheet towards an inside based on a widthwise folding line in a widthwise direction perpendicular to the longitudinal direction; and a third step of folding, after the first step, a widthwise end region of the absorbent article including each of both ends in the widthwise direction of the absorbent article, and the packaging sheet towards the inside based on a longitudinal folding line in the longitudinal direction.

DESCRIPTION OF EMBODIMENTS

First Embodiment

Figure 1:
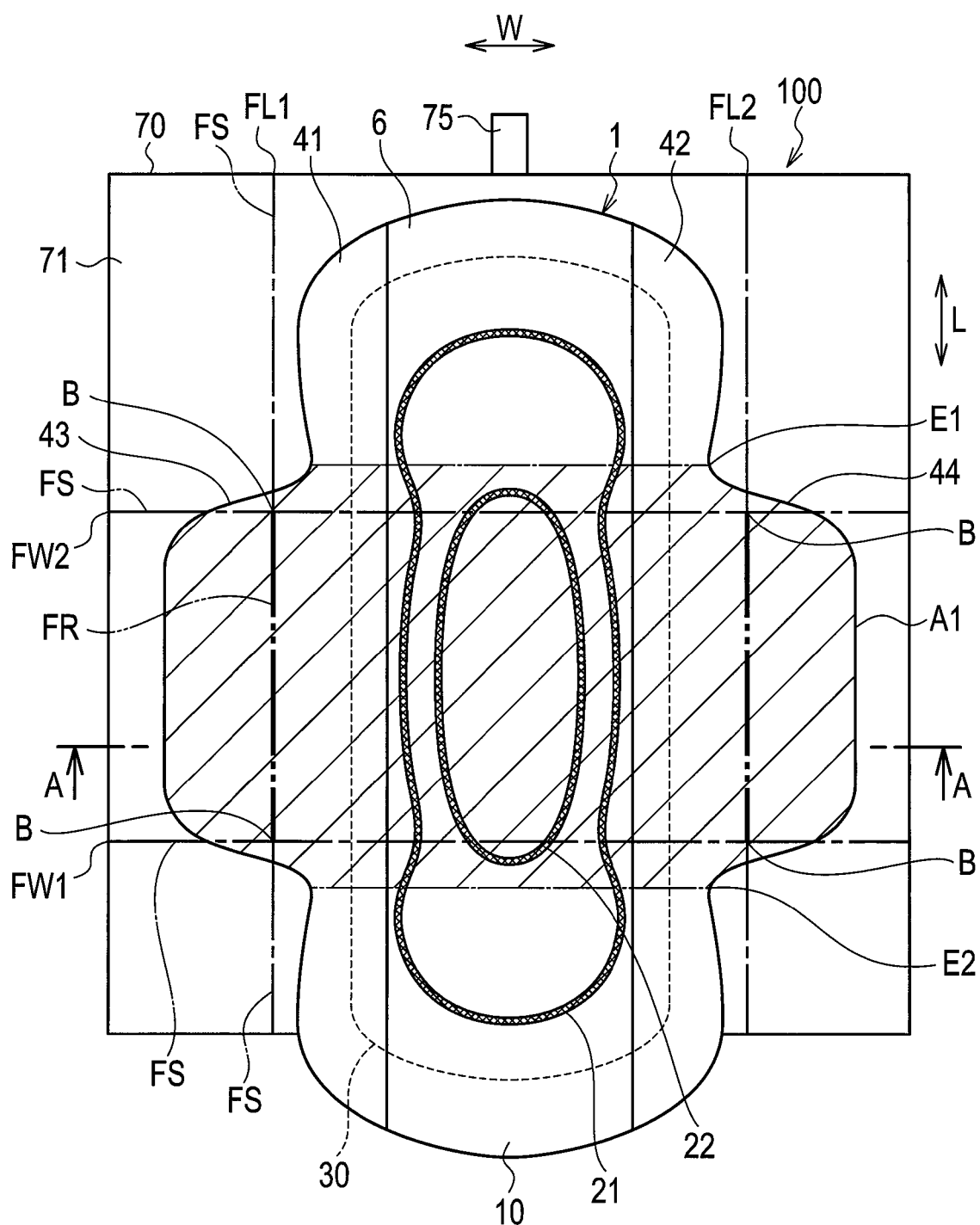
FIG. 1 is a plan view as seen from a skin contact surface side of an absorbent article package according to a first embodiment of the present invention.
Figure 2:
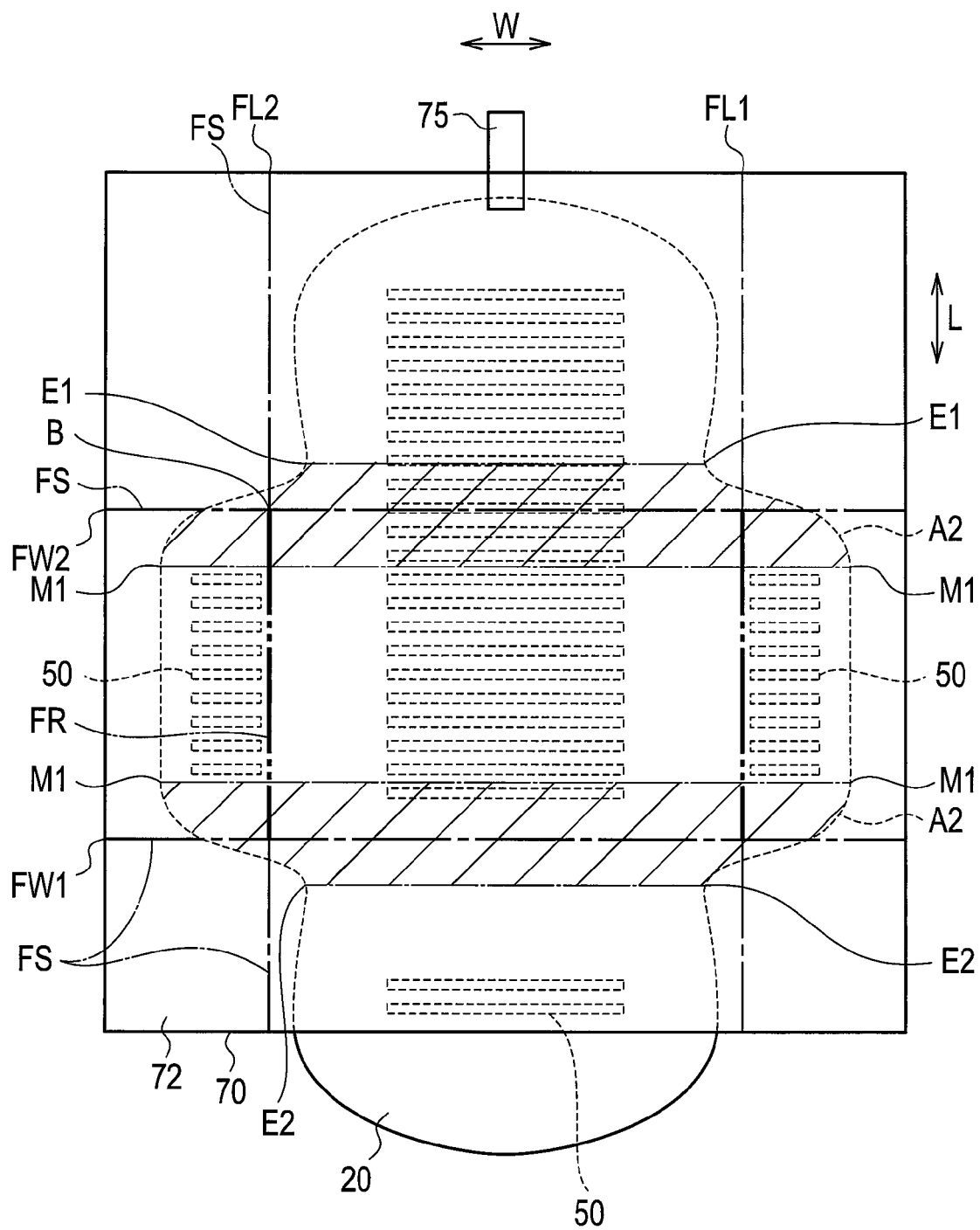
FIG. 2 is a back view of the absorbent article package shown in FIG. 1.

With reference to FIGS. 1 and 2, an absorbent article package according to a first embodiment of the present invention will be explained. FIG. 1 is a plan view of the absorbent article package, and FIG. 2 is a back view of the absorbent article package. As shown in FIGS. 1 and 2, an absorbent article package 100 has an absorbent article 1 and a packaging sheet 70 in which the absorbent article 1 is individually packaged. The absorbent article 1 according to the present embodiment is a sanitary napkin, for example.

The absorbent article package 100 is configured so that the absorbent article 1 is individually packaged by folding the packaging sheet 70 and the absorbent article 1 in a state where the absorbent article 1 is arranged on the packaging sheet 70. FIGS. 1 and 2 illustrate a state in which after the absorbent article 1 is individually packaged in the packaging sheet 70, the individually-packaged absorbent article 1 is opened.

The absorbent article 1 has a topsheet 10 configured to come in contact with the skin of a wearer, a liquid-impermeable backsheet 20 that does not allow liquid to pass through, and an absorber 30. The absorber 30 is disposed between the topsheet 10 and the backsheet 20. Therefore, the absorber 30 is illustrated with a dashed line in FIG. 1. The absorber 30 is disposed in the center part in a longitudinal direction L and a widthwise direction W of the absorbent article 1. In the plan view shown in FIG. 1, the absorbent article 1 has the absorber 30, and includes an absorbent main body 6 extending in the longitudinal direction L and wing units 43, 44 provided outside the absorbent main body 6 in the widthwise direction W perpendicular to the longitudinal direction L. Furthermore, the absorbent article 1 includes sidesheets 41, 42 provided outside the absorber 30 in the widthwise direction W.

The topsheet 10 is a liquid-permeable sheet that allows liquid such as bodily fluid to pass through. The topsheet 10 covers at least the surface of the absorber 30. The topsheet 10 is not particularly limited as long as the topsheet 10 is a sheet-like material having a structure that allows liquid to pass through, such as a nonwoven fabric, a woven fabric, a perforated plastic sheet, and a mesh sheet. As a woven fabric and a nonwoven fabric, both a natural fiber and a chemical fiber can be used.

The backsheet 20 has substantially the same length as a length of the topsheet 10. As for the backsheet 20, a film having a main constituent such as polyethylene; polypropylene an air-permeable resin film; a sheet in which an air-permeable resin film is joined to a nonwoven fabric such as spunbond or spun lace; or the like can be used. The backsheet 20 is desired to be of a material having flexibility to an extent such that a feeling of discomfort is not given at the time of wearing.

The absorber 30 includes a hydrophilic fiber and pulp. The absorber 30 may be formed by layering a hydrophilic fiber or a powder by an air-laid method, or the absorber 30 may be an air-laid sheet in which a hydrophilic fiber or a powder is shaped into a sheet-like form by an air-laid method. The sidesheets 41, 42 may be selected from similar materials to that of the topsheet 10. However, in order to prevent menstrual blood from flowing to the outside of the disposable articlel by crossing over the sidesheets 41, 42, it is desirable that the material has a hydrophobic property or water repellency.

The sidesheets 41, 42 are disposed at the both sides of the topsheet 10. The sidesheets 41, 42 cover a part of the side edges of the absorber 30, and the wing units 43, 44. In the absorbent article 1, the peripheries of the topsheet 10, the sidesheets 41, 42, and the backsheet 20 are joined, and the absorber 30 is sealed therein. As a method of joining the topsheet 10 and the backsheet 20, anyone or a combination of heat embossing, supersonic waves, and a hot-melt adhesive can be used.

In the backsheet 20, a surface which comes in contact with underwear is provided with a plurality of application regions 50 applied with an adhesive (see FIG. 2). The plurality of application regions 50 are provided so as to extend in the widthwise direction. The plurality of application regions 50 are arranged intermittently in the longitudinal direction L of the backsheet 20. In each of the wing units 43, 44, this application region 50 is provided on the surface which comes in contact with a underwear. In a state before use, an adhesive is in contact with the packaging sheet 70 so that the packaging sheet 70 prevents the adhesive from deteriorating before use. The packaging sheet 70 is released by a wearer at the time of use. It may be configured so as to prevent the adhesive from deteriorating before use, by means of a protection sheet made of a paper or the like, other than the packaging sheet 70.

The topsheet 10 is provided with a plurality of compressed grooves 21, 22. The compressed grooves 21, 22 are configured by compressing from the topsheet 10 to the absorber 30 in the thickness direction. In the present embodiment, the compressed grooves 21, 22 are compression-processed by an embossing process.

The packaging sheet 70 has the absorbent article 1 individually packaged therein. The packaging sheet 70 has a facing surface 71 which faces to the absorbent article 1 at the backsheet 20 side of the absorbent article 1, and a non-facing surface 72 which is positioned outside in a state where the absorbent article 1 is housed.

In the packaging sheet 70, it is to be noted that the surface of the packaging sheet 70 may be surface-processed by a round-spot embossing, a crepe embossing, or the like, for the purpose of improvement in its texture. Given as a material for the packaging sheet 70 are various types of films such as a plastic film such as polyethylene, polypropylene, or polyester, a nylon film, and the like; an air-permeable film stretched with the use of filler such as barium sulphate; a film obtained by laminating nonwoven fabrics; and the like. Furthermore, the surface of the packaging sheet 70 is processed so as to be releasable without decreasing viscosity of the adhesive.

The absorbent article 1 and the packaging sheet 70 are folded along predetermined folding positions in the widthwise direction W and the longitudinal direction L with the topsheet 10 of the absorbent article 1 being inside. In a state where the absorbent article 1 is folded, one end in the longitudinal direction L of the packaging sheet 70 is pasted to the packaging sheet 70. The end of the packaging sheet 70 is pasted to a part of the packaging sheet 70 by means of an adhesive tape 75.

Next, a method of folding the absorbent article package 100 will be explained. FIGS. 3 to 6 are perspective views schematically showing a step of folding the absorbent article package 100. The step of folding the absorbent article package 100 has an absorbent-article-arranging step S1, a first folding step S2, a second folding step S3, a joining step S4, and a third folding step S5.

Figure 3:
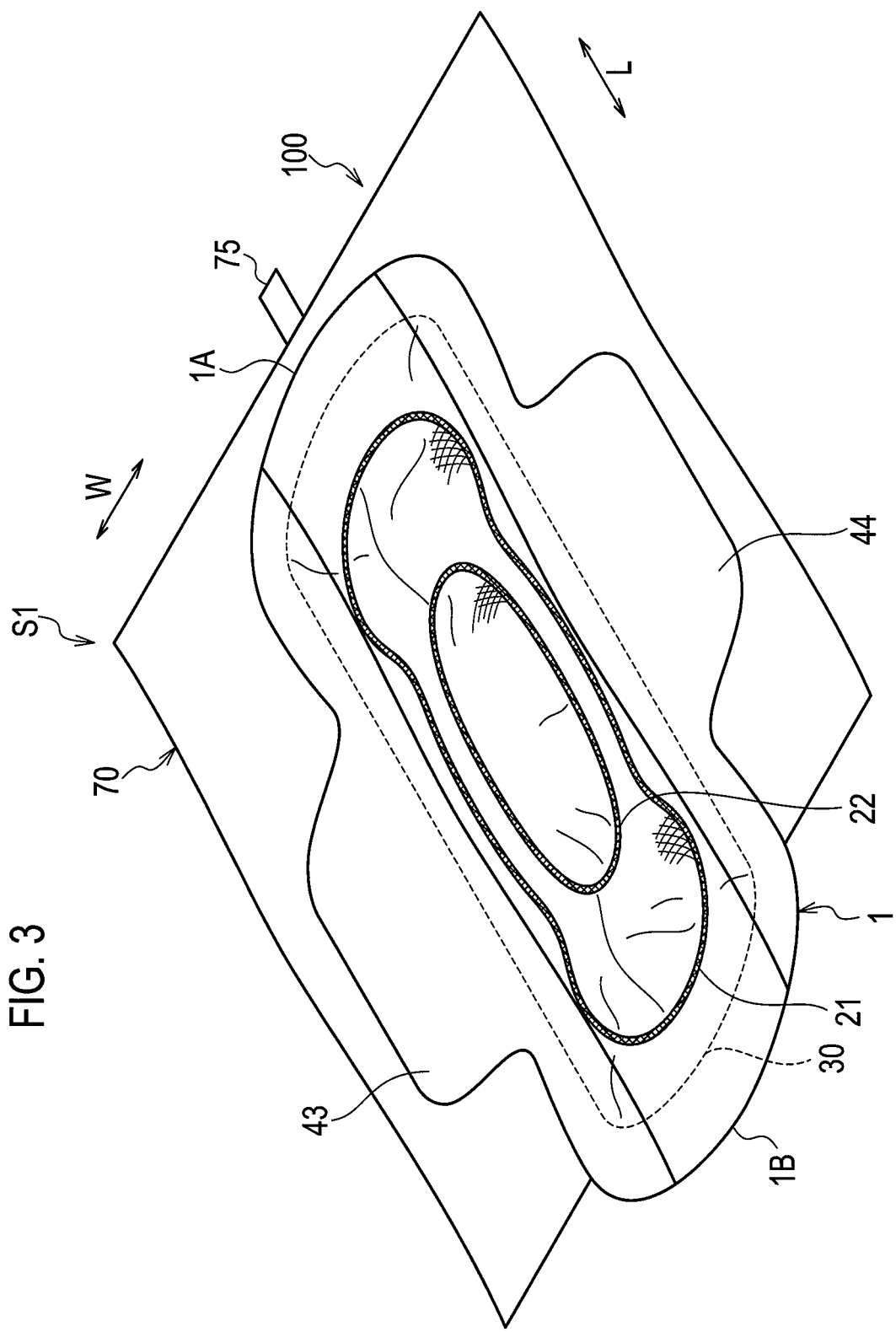
FIG. 3 is a perspective view schematically showing an absorbent-article-arranging step during a step of folding the absorbent article package shown in FIG. 1.

In the absorbent-article-loading step S1, as shown in FIG. 3, the absorbent article 1 is arranged on the packaging sheet 70. The packaging sheet 70 and the backsheet 20 of the absorbent article 1 face to each other. In FIG. 3, the absorbent article 1 is arranged on the packaging sheet 70 having a size for individual packaging of the single absorbent article 1. For example, it may be configured that absorbent articles 1 may be arranged at a predetermined interval on a packaging sheet 70 which is continuous in the conveyance direction. In the present embodiment, for convenience of explanation, a folding method will be explained with reference to the package of the single absorbent article.

Figure 4:
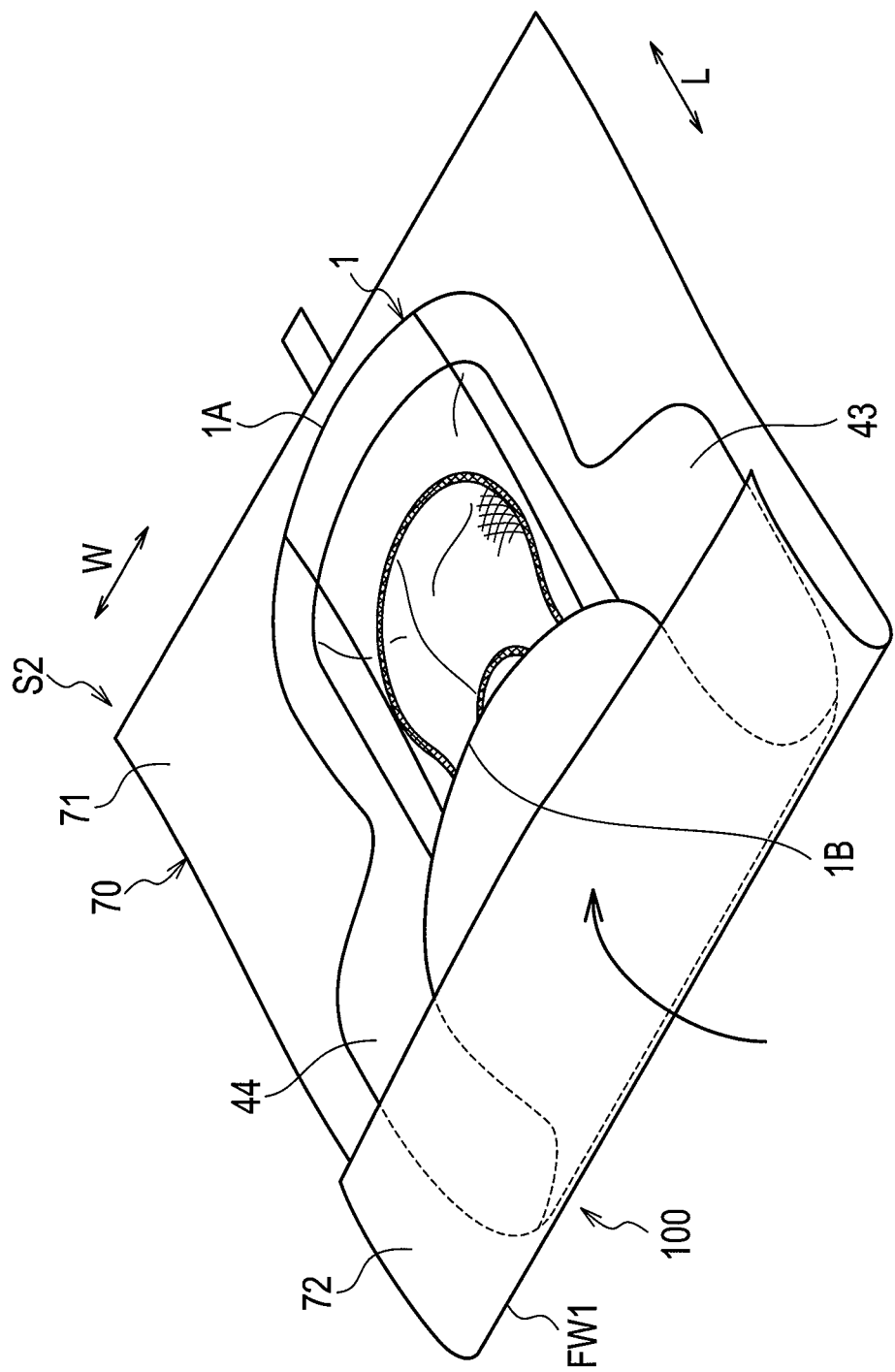
FIG. 4 is a perspective view schematically showing a first folding step during the step of folding the absorbent article package shown in FIG. 1.

In the first folding step S2, as shown in FIG. 4, the packaging sheet 70 and the absorbent article 1 are folded back towards the inside from an end region side including either one of the both ends 1A, 1B in the longitudinal direction of the absorbent article 1, based on a first widthwise folding line (see FIG. 1) FW1 along the widthwise direction W. Herein, either one of the both ends 1A, 1B in the longitudinal direction of the absorbent article 1 is, in particular, a rear end 1B to be arranged at a rear part of a wearer. It is to be noted that either one of the both ends 1A, 1B in the longitudinal direction of the absorbent article 1 may be, for example, a front end 1A to be arranged at a front side of the wearer, and it may be configured to fold back from the end region side including the front end 1A side in the first folding step.

Figure 5:
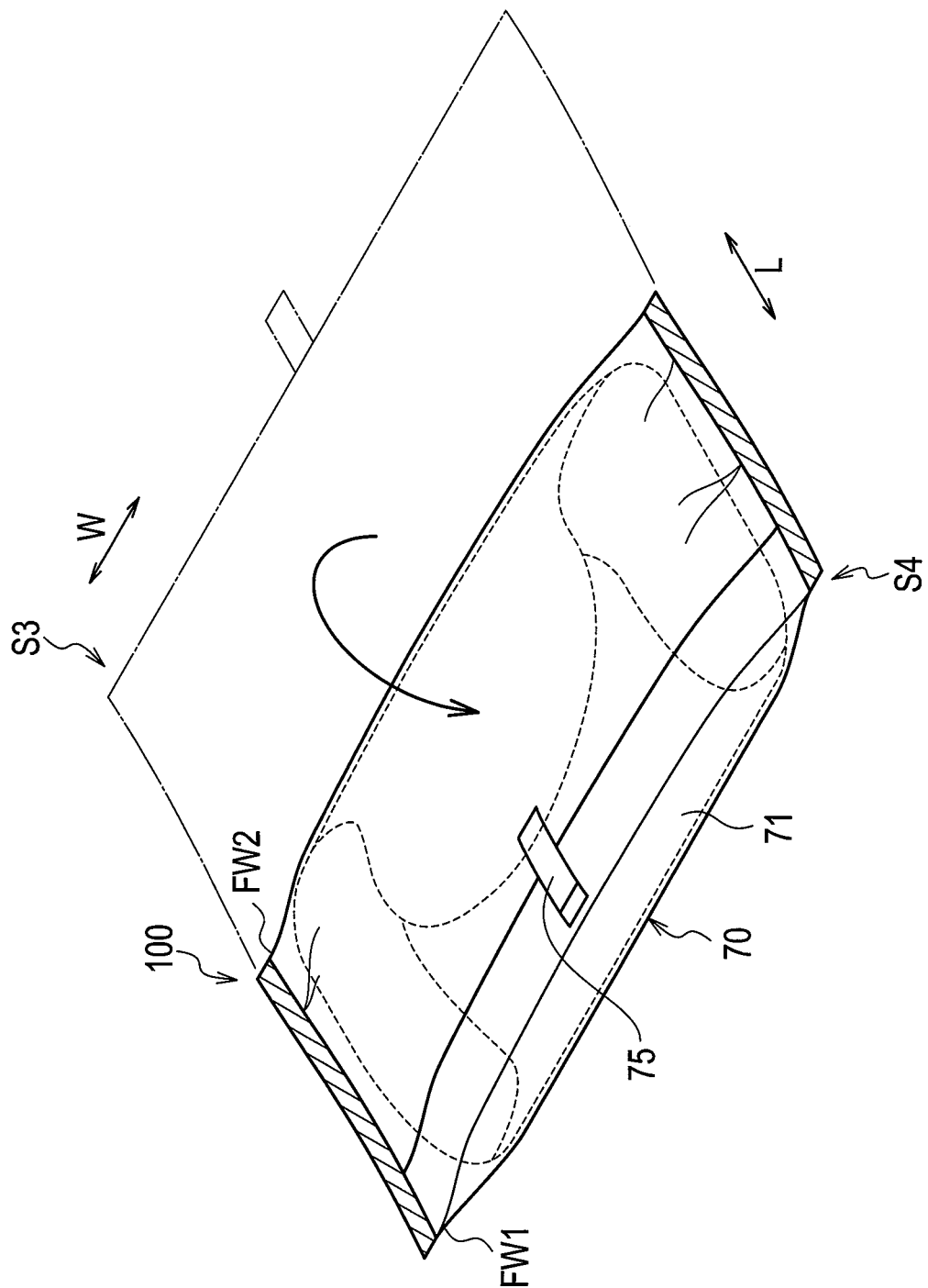
FIG. 5 is a perspective view schematically showing a second folding step and a joining step during the step of folding the absorbent article package shown in FIG. 1.

In the second folding step S3, as shown in FIG. 5, the packaging sheet 70 and the absorbent article 1 are folded back towards the inside from the front end 1A side in the longitudinal direction L of the absorbent article 1, based on a second widthwise folding line FW2 (see FIG. 1) along the widthwise direction W.

Figure 6:
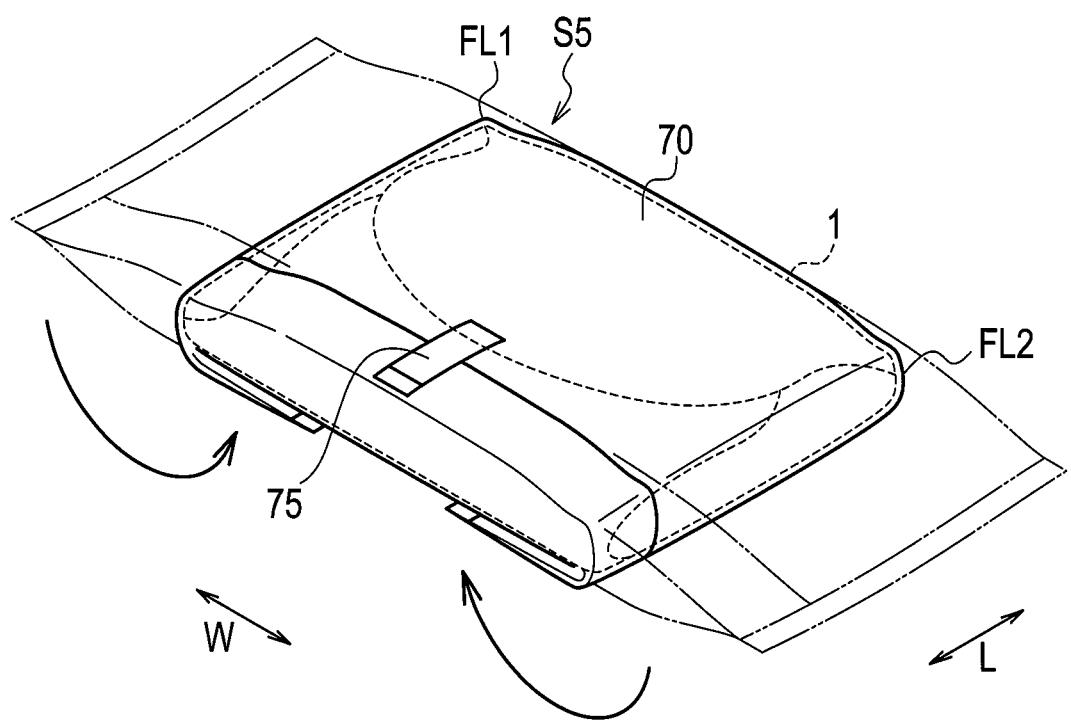
FIG. 6 is a perspective view schematically showing a third folding step during the step of folding the absorbent article package shown in FIG. 1.

In the joining step S4, as shown in FIG. 6, the both ends in the widthwise direction of the absorbent article 1 and the packaging sheet 70 folded back based on the first widthwise folding line FW1 and the second widthwise direction folding line FW2 are bonded by means of thermal welding. The shaded part shown in FIG. 5 is a region bonded by means of thermal welding. Subsequently, the end of the packaging sheet 70 is pasted to the non-facing surface 72 of the packaging sheet 70 by means of the adhesive tape 75. Through this step, the absorbent article 1 is individually packaged in the packaging sheet 70.

In the present embodiment, the both ends in the widthwise direction of the absorbent article 1 and the packaging sheet 70 folded back based on the first widthwise folding line FW1 and the second widthwise direction folding line FW2 are bonded by means of thermal welding. However, the both ends in the widthwise direction of the absorbent article 1 and the packaging sheet 70 may not be bonded. Furthermore, as a method of bonding the both ends in the widthwise direction of the absorbent article 1 and the packaging sheet 70, bonding may be performed by pressure bonding or ultrasonic welding.

In the third folding step S5, as shown in FIG. 6, the packaging sheet 70 and the absorbent article 1 are folded back towards the inside from the both end sides in the widthwise direction W of the absorbent article 1, based on a first longitudinal folding line FL1 and a second longitudinal folding line FL2 (see FIG. 1) along the longitudinal direction L. Upon execution of the steps S1 to S5 described above, the absorbent article package 100 is folded and reduced in its size.

At the time of folding back the packaging sheet 70 and the absorbent article 1 from the both end sides in the widthwise direction W of the absorbent article 1, it may be configured to fold back from one of the end sides in the widthwise direction W at a time or to fold back the both end sides in the widthwise direction W at a time.

By folding as described above, the absorbent article 1 can be individually packaged in a compact size in the packaging sheet 70. Owing to size reduction of the absorbent article 1, in a case of storing it in a bag such as a pouch, there is no need to occupy a large storage space inside the bag, which makes it easy to carry around. Furthermore, owing to individual packaging of the absorbent article 1 in a compact size, at the time of carrying it to a bathroom for use, the absorbent article 1 can be held out of sight of others by placing it in hand even in an unfolded state.

Figure 7:
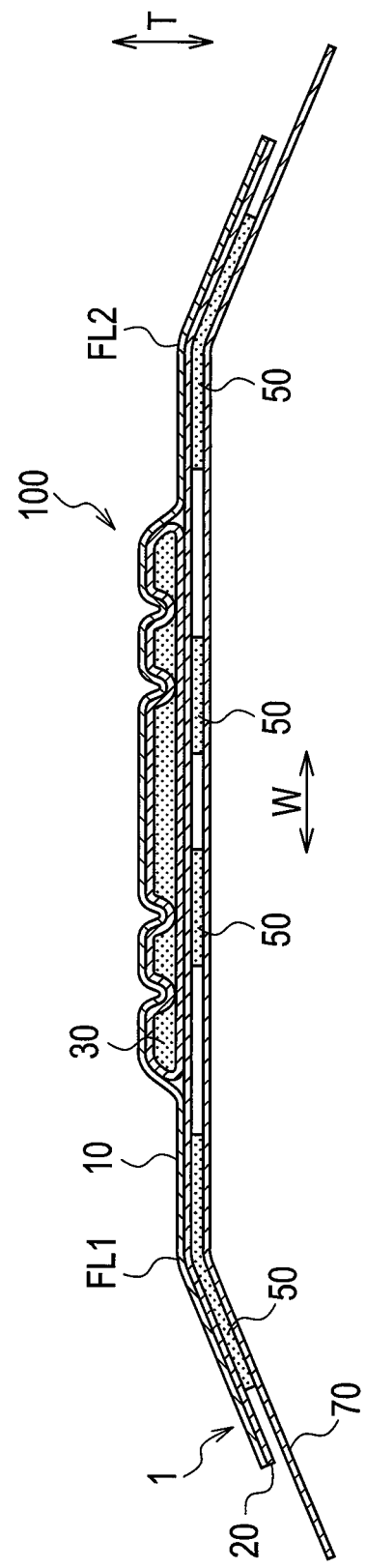
FIG. 7 is a cross-sectional view taken along a line A-A shown in FIG. 1.

Subsequently, folding lines in a state where the absorbent article package 100 thus folded is opened will be explained with reference to FIGS. 1, 2, and 7. FIG. 7 is a cross-sectional view taken along a line A-A shown in FIG. 1. A dashed line and a chain double-dashed line shown in FIGS. 1 and 2 are virtual lines indicative of a folding line. The dashed line indicates a first folding line FS based on which the absorbent article 1 and the packaging sheet 70 are folded back towards the topsheet 10 side of the absorbent article 1. Furthermore, the chain double-dashed line indicates a second folding line FR based on which the absorbent article 1 and the packaging sheet 70 are folded back towards the backsheet 20 side of the absorbent article 1.

In the absorbent article 1 and the packaging sheet 70, the first longitudinal folding line FL1 and the second longitudinal folding line FL2 along the longitudinal direction L of the absorbent article 1, and the first widthwise folding line FW1 and the second widthwise folding line FW2 along the widthwise direction W of the absorbent article 1 are formed.

Both of the first widthwise folding line FW1 and the second widthwise folding line FW2 correspond to the first folding line FS folded back towards the topsheet side of the absorbent article 1. Therefore, in a state where the absorbent article 1 is opened, the both ends in the longitudinal direction L are folded back towards the topsheet 10 side with respect to the center region in the longitudinal direction L (the region inside the first widthwise folding line FW1 and the second widthwise folding line FW2 in the longitudinal direction).

The first longitudinal folding line FL1 and the second longitudinal folding line FL2 have the first folding lines FS and the second folding lines FR arranged adjacent to each other in the longitudinal direction L. Specifically, the first folding lines FS are formed at the both ends in the longitudinal direction and the second folding lines FR are formed between the first folding lines FS.

A boundary B between the first folding line FS and the second folding line FR in each of the first longitudinal folding line FL1 and the second longitudinal folding line FL2 is formed within a region between the both sides in the widthwise direction of the wing units 43, 44 as well as a region (hereinafter, referred to as a wing unit corresponding region) A1 between the both ends E1, E2 in the longitudinal direction of the wing units. The wing unit corresponding region A1 corresponds to a shaded part shown in FIG. 1.

In each of the first longitudinal folding line FL1 and the second longitudinal folding line FL2 formed in the wing unit corresponding region A1, the first folding line FS, the second folding line FR, and the first folding line FS are formed in this order along the longitudinal direction L.

Because the first folding lines FS and the second folding lines FR are formed in the wing unit corresponding region A1 by providing the boundaries B between the first folding lines FS and the second folding lines FR in the wing unit corresponding region A1, bending towards only one side (for example, the topsheet 10 side) can be prevented by the action of the both folding lines, thereby making it difficult to leave a folding pattern. Therefore, at the time of opening the absorbent article 1 folded in a compact size, the absorbent article 1 can be easily kept horizontal. A wearer can easily arrange the absorbent article 1 along the inner surface of underwear or arrange the absorbent article 1 by easily bending over the wing units 43, 44 to a non-contact surface side of the underwear, which improves the fitting. Furthermore, by making it difficult to leave a folding pattern, at the time of installing the absorbent article 1 on underwear, the absorbent article 1 can be prevented from floating up from the underwear due to the folding lines.

Furthermore, in the wing unit corresponding region A1, a length in the longitudinal direction of the second folding line FR is greater than a length in the longitudinal direction of the first folding line FS. As shown in FIG. 1, the wing units 43, 44 positioned outside the second folding lines FR in the widthwise direction are folded towards the backsheet side. Therefore, by making the second folding lines FR longer, the wing units 43, 44 are more likely to bend towards the backsheet 20 side than the topsheet 10 side.

For example, in a case where the wing units 43, 44 are folded back towards the topsheet side, force is exerted in the direction of separating from the backsheet 20 at the time of installation on underwear, thereby causing a possibility that the wing units 43, 44 are installed out of position or the installed wing units 43, 44 are separated from the underwear. However, by making the second folding lines FR longer, a wearer can fold back the wing units 43, 44 towards the backsheet side in a proper position.

Furthermore, in the wing unit corresponding region A1, the first folding line FS is formed at the outside in the longitudinal direction with respect to each of the both ends in the longitudinal direction of the second folding line FR. For example, if the second folding line FR is formed in the entire region of the wing unit corresponding region A1, the wing units 43, 44 come close to the backsheet 20 of the absorbent article 1 at the time of removing the absorbent article 1 from the packaging sheet 70, thereby causing a possibility that the adhesive of the wing units 43, 44 and the adhesive of the absorbent main body 6 are bonded together. However, in the wing unit corresponding region A1, by forming the first folding line FS at each of the both ends in the longitudinal direction of the second folding line FR, force is exerted by the first folding line FS, in the direction of separating the wing units 43, 44 from the backsheet 20 side, thereby making it possible to prevent the wing units 43, 44 from being bonded to the backsheet 20.

Furthermore, in the first longitudinal folding line FL1 and the second longitudinal folding line FL2, the boundary B between the first folding lines FS and the second folding lines FR are formed in a region between the both sides in the widthwise direction of the wing units 43, 44 as well as regions (wing inclined regions) A2 in the longitudinal direction, between the maximum width position having the greatest length in the widthwise direction of the wing units 43, 44 and the both ends E1, E2 in the longitudinal direction of the wing units 43, 44. The wing inclined regions A2 correspond to shaded parts shown in FIG. 2.

It is to be noted that the maximum width positions M1 having the greatest length in the widthwise direction of the wing units 43, 44, which divide the wing inclined regions A2, correspond to parts positioned at the outermost sides in the longitudinal direction of the part at the maximum width position. The wing units 43, 44 positioned at the outside in the longitudinal direction of this maximum width position have a length in the widthwise direction which gets gradually shorter towards the outside in the longitudinal direction so as to be inclined with respect to the widthwise direction W and the longitudinal direction L.

In the wing units 43, 44, the thickness is smaller as compared to the absorbent main body 6 having the absorber 30, so that wrinkles are relatively easy to occur. Furthermore, the adhesives is provided to the back surface of the wing units 43, 44, and there is a case in which the adhesive is stuck together at the time of folding back the wing units 43, 44 towards the non-contact surface side of underwear, resulting in wrinkles in the wing units 43, 44. However, formation of the boundaries B between the first folding lines FS and the second folding lines FR in the wing inclined regions A2 enables the wing units 43, 44 to be kept horizontal in the longitudinal direction by the action of the first folding lines FS and the second folding lines FR, thereby being able to prevent a problem of wrinkles from occurring in the wing units 43, 44.

In the first embodiment, the first folding line FS and the second folding line FR are arranged continuously. However, a gap may be formed between the first folding line FS and the second folding line FR.

Furthermore, in the present embodiment, the first longitudinal folding line FL1 and the second longitudinal folding line FL2 are formed on the wing units 43, 44. However, a position of the first longitudinal folding line FL1 and the second longitudinal folding line FL2 is not limited to this configuration. For example, the first longitudinal folding line FL1 and the second longitudinal folding line FL2 may be formed at the inside in the widthwise direction of the wing units 43, 44. Furthermore, the first longitudinal folding line FL1 and the second longitudinal folding line FL2 may be formed at the outside in the widthwise direction of the absorber 30 or may be formed in a position superimposed on the absorber 30.

Second Embodiment

Figure 8:
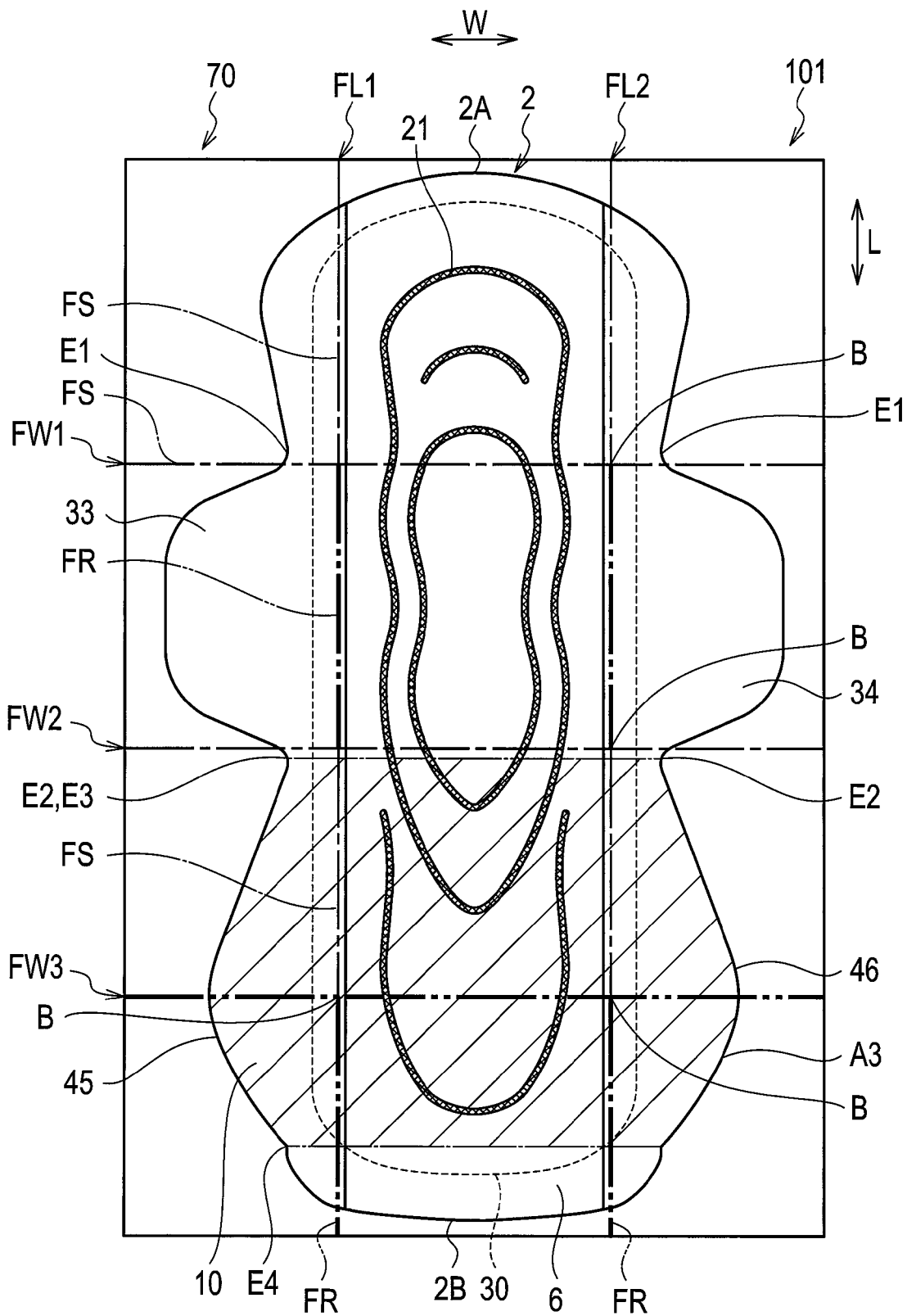
FIG. 8 is a plan view as seen from a skin contact surface side of an absorbent article package according to a second embodiment of the present invention.

Next, an absorbent article package 101 according to a second embodiment will be described in details with reference to FIG. 8. In the explanation of the second embodiment, only the configuration that is different from the first embodiment will be explained while omitting the explanation of the same configuration. FIG. 8 is a plan view as seen from a skin contact surface the absorbent article package 101 according to the second embodiment.

An absorbent article 2 according to the second embodiment is different from the absorbent article 1 according to the first embodiment in that end flap units 45, 46 projecting to the outside in the widthwise direction of the absorber main body 6 are included in a rear region of the absorbent article 2. Furthermore, in the absorbent article package 101, the first longitudinal folding line FL1 and the second longitudinal folding line FL2 along the longitudinal direction L of the absorbent article 2, and the first widthwise folding line FW1, the second widthwise folding line FW2, and a third widthwise folding line FW3 along the widthwise direction W of the absorbent article 2 are formed.

Both of the first widthwise folding line FW1 and the second widthwise folding line FW2 correspond to the first folding line FS based on which the absorbent article 2 and the packaging sheet 70 are folded back towards the topsheet 10 side of the absorbent article 2. On the other hand, the third widthwise direction folding line FW3 corresponds to the second folding line FR based on which the absorbent article 2 and the packaging sheet 70 are folded back towards the backsheet 20 side of the absorbent article 2.

In the first longitudinal folding line FL1 and the second longitudinal folding line FL2, the first folding lines FS and the second folding lines FR are formed adjacent to each other along the longitudinal direction L. Specifically, along the longitudinal direction of the absorbent article, the first folding line FS, the second folding line FR, the first folding line FS, and the second folding line FR are formed in this order from a region including a front end of the absorbent article.

Boundaries B between the first folding lines FS and the second folding lines FR are formed in a region between the both sides in the widthwise direction of the end flap units 45, 46 as well as a region (hereinafter, referred to as an end flap unit corresponding region) A3 between both ends E3, E4 in the longitudinal direction of the end flap units, and a wing unit corresponding region A1. The end flap unit corresponding region A3 corresponds to a shaded part shown in FIG. 8. In the present embodiment, a rear end E2 in the longitudinal direction of the wing units 43, 44 and the front end E3 in the longitudinal direction of the end flap units 45, 46 are placed at the same position.

As described above, in the first longitudinal folding line FL1 and the second longitudinal folding line FL2, because the boundaries B between the first folding lines FS and the second folding lines FR are provided in the end flap unit corresponding region A3, bending towards only one side (for example, the topsheet 10 side) can be prevented by the action of the both folding lines, thereby making it difficult to leave a folding pattern, so that the end flap unit corresponding region A3 can be easily kept horizontal. By keeping the end flap unit corresponding region A3 horizontal, the end flap units 45, 46 can be appropriately arranged along the inner surface of underwear.

It is to be noted that the absorbent article package 101 shown in FIG. 8 is in a state where the absorbent article 2 which has been individually packaged is opened after individual packaging of the absorbent article 2 using the packaging sheet 70. As a method of folding the absorbent article package 101, for example, after arranging the absorbent article 2 on the packaging sheet 70, the rear region including a rear end 2B of the absorbent article 2 is folded towards the inside with respect to the front region including a front end 2A of the absorbent article 2 based on the second widthwise folding line FW2.

Subsequently, the absorbent article 2 and the packaging sheet 70 are folded based on the first widthwise folding line FW1 and the third widthwise folding line FW3 in a state where the rear region including the rear end 2B of the absorbent article 2 is superimposed on the front region including the front end 2A of the absorbent article 2. Subsequently, after the both ends in the widthwise direction of the packaging sheet 70 are joined together and an adhesive tape 75 is pasted, the both ends in the widthwise direction of the packaging sheet 70 and the absorbent article 2 are folded towards the inside based on the first longitudinal folding line FL1 and the second longitudinal folding line FL2. By folding in this manner, the absorbent article 1 is individually packaged in the packaging sheet 70, and the state shown in FIG. 8 is established by opening the individually-packaged absorbent article 2.

In the absorbent article package 101 according to the second embodiment, the first widthwise folding line FW1, the second widthwise folding line FW2, and the third widthwise folding line FW3 in the widthwise direction W of the absorbent article 2 are formed. However, the number of widthwise folding lines is not limited to this configuration. Furthermore, the boundaries between the first folding lines FS and the second folding lines FR are not necessarily formed in the wing unit corresponding region A1 or the end flap unit corresponding region A3.

Figure 9:
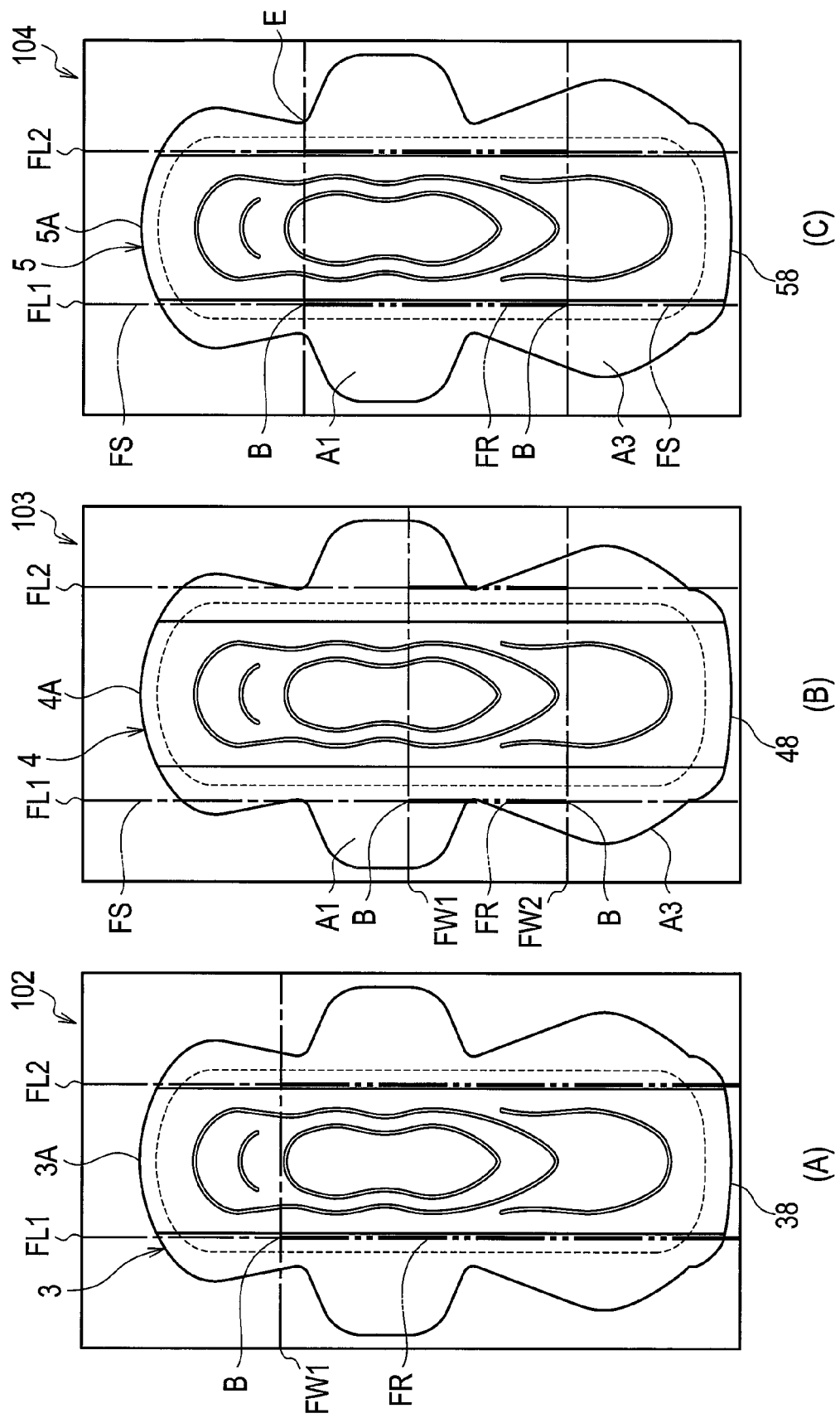
FIG. 9 shows plan views as seen from a skin contact surface side of an absorbent article package according to modifications.

Subsequently, absorbent article packages according to modifications will be explained with reference to FIG. 9. FIG. 9(a) is a plan view as seen from a skin contact surface side of an absorbent article package according to a first modification; FIG. 9(b) is a plan view as seen from a skin contact surface side of an absorbent article package according to a second modification; and FIG. 9(c) is a plan view as seen from a skin contact surface side of an absorbent article package according to a third modification. In the explanation of the modifications, only the configuration that is different from the second embodiment will be explained while omitting the explanation of the same configuration.

In a package 102 of an absorbent article 3 according to the first modification, the first longitudinal folding line FL1 and the second longitudinal folding line FL2 along the longitudinal direction L of the absorbent article 3, and the first widthwise folding line FW1 along the widthwise direction W of the absorbent article 3 are formed. In the first longitudinal folding line FL1 and the second longitudinal folding line FL2, the first folding lines FS and the second folding lines FR are formed. In a region including a front end 3A of the absorbent article 3, the first folding lines FS are formed while in a region including a rear end 3B of the absorbent article 3, the second folding lines FR are formed.

In the package 103 of an absorbent article 4 according to the second modification and a package 104 of an absorbent article 5 according to the third modification, the first longitudinal folding line FL1 and the second longitudinal folding line FL2 along the longitudinal direction L are formed. In the first longitudinal folding line FL1 and the second longitudinal folding line FL2, the first folding line FS, the second folding line FR, and the first folding line FS are formed in this order along the longitudinal direction L.

Furthermore, the boundaries B between the first folding lines FS and the second folding lines FR in the second modification are formed in the wing unit corresponding region A1 and the end flap unit corresponding region A3. On the other hand, the boundaries B between the first folding lines FS and the second folding lines FR in the third modification are provided in a position superimposed on the front end E1 of the wing units. Furthermore, the first longitudinal folding line FL1 and the second longitudinal folding line FL2 in the third modification are formed in a position superimposed on the absorber 30.

Figure 10:
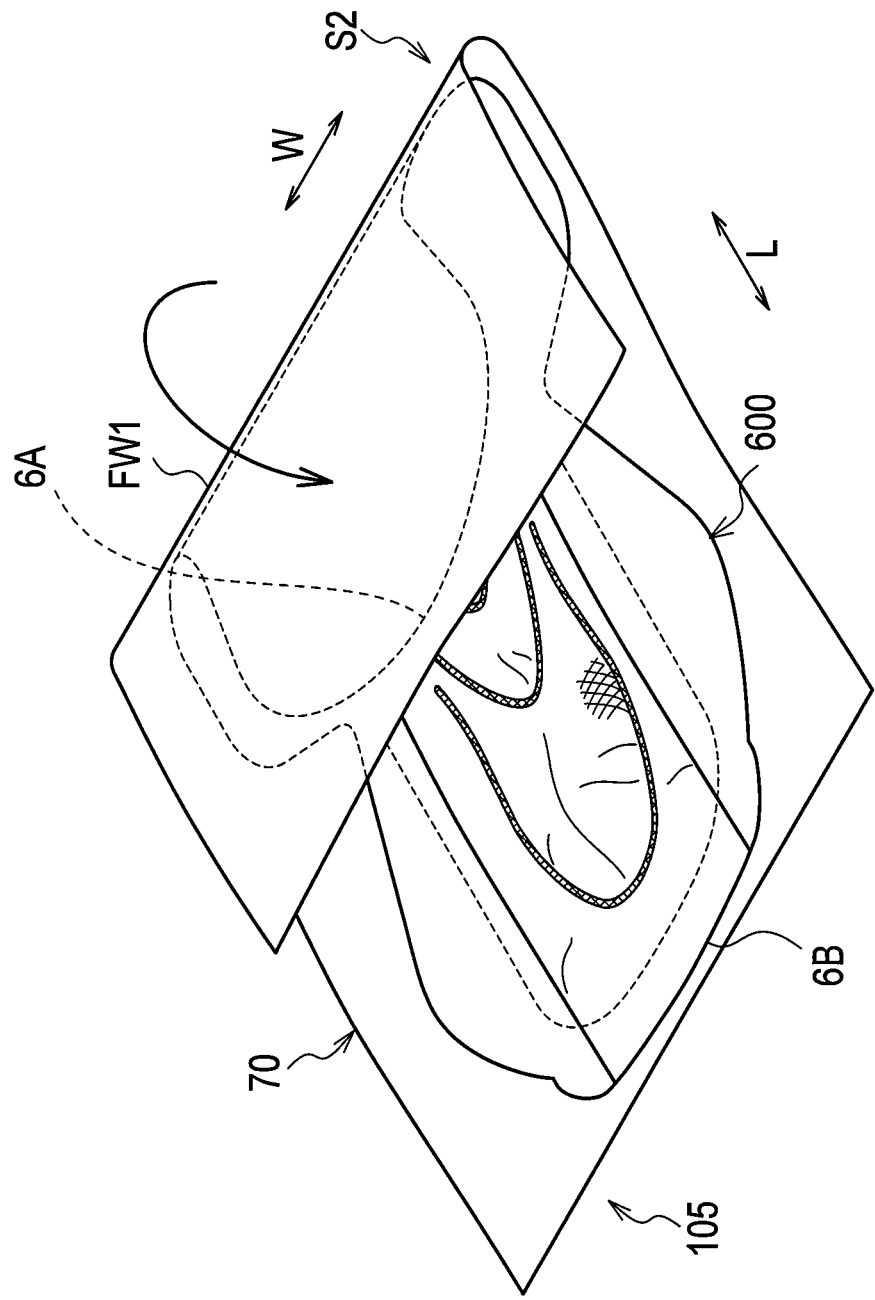
FIG. 10 is a perspective view schematically showing a first folding step and a pasting step during a step of folding the absorbent article package according to the modification.
Figure 11:
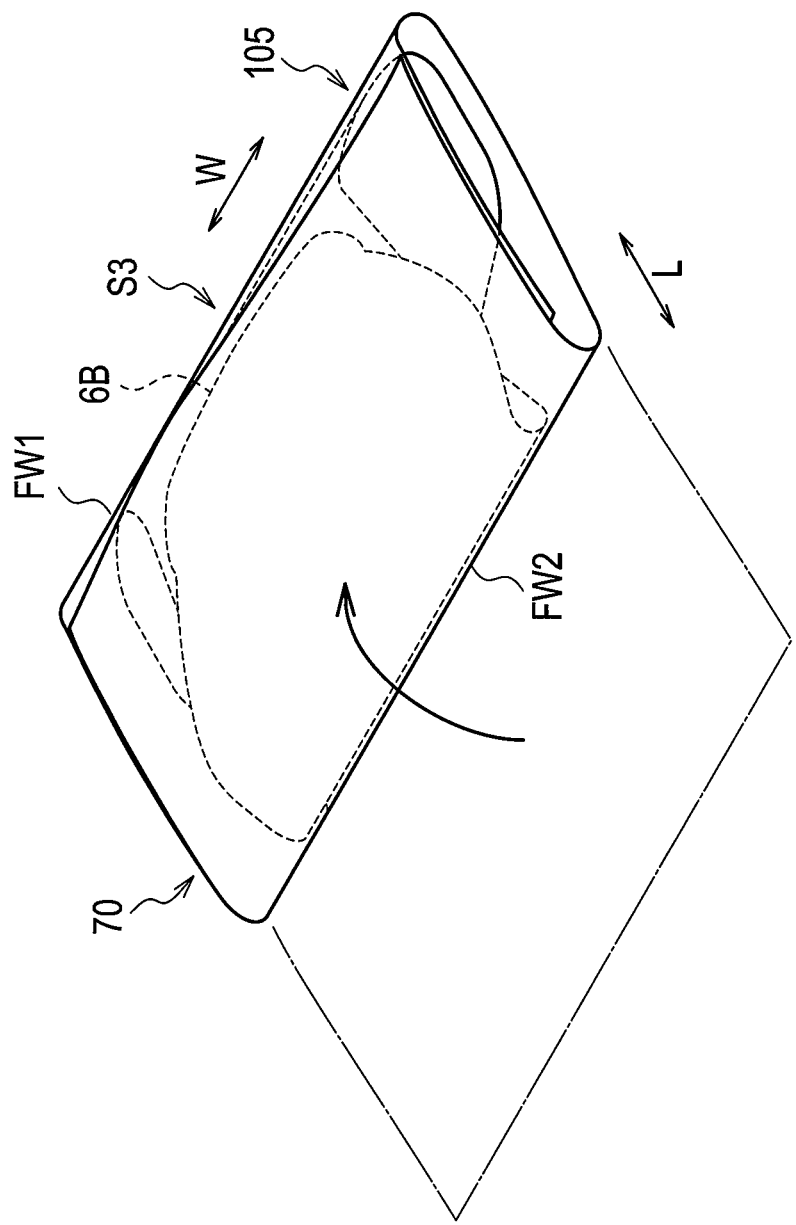
FIG. 11 is a perspective view schematically showing a second folding step during the step of folding the absorbent article package according to the modification.
Figure 12:
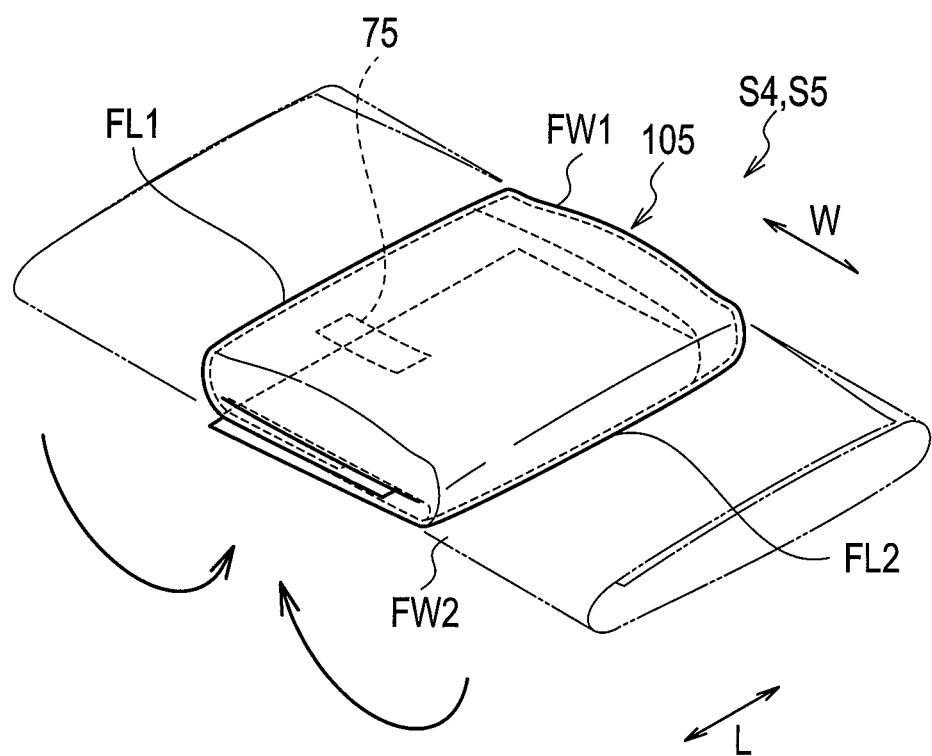
FIG. 12 is a perspective view schematically showing a third folding step during the step of folding the absorbent article package according to the modification.

Subsequently, a method of folding the package 105 of the absorbent article according to the modifications will be explained. FIGS. 10 to 12 are perspective views each schematically showing a step of folding the absorbent article package 105. The step of folding the absorbent article package 105 has an absorbent-article-loading step S1, a first folding step S2, a second folding step S3, a third folding step S4, and a joining step S5. However, the absorbent-article-loading step S1 is the same as that of the folding step according to the embodiment, so that its explanation will be omitted.

In the first folding step S2, as shown in FIG. 10, the packaging sheet 70 and the absorbent article 600 are folded back towards the inside from an end region side including a front end 6A that is either one of both ends 6A, 6B in the longitudinal direction of an absorbent article 6, based on the first widthwise folding line FW1 in the widthwise direction W.

In the second folding step S3, as shown in FIG. 11, the packaging sheet 70 and the absorbent article 600 are folded back towards the inside from an end region side including a rear end 6B that is either one of the both ends 6A, 6B in the longitudinal direction of the absorbent article 6, based on the second folding line FW2 in the widthwise direction W.

In the third folding step S4, as shown in FIG. 12, the packaging sheet 70 and the absorbent article 600 are folded back towards a rear surface side from the both end sides in the widthwise direction W of the absorbent article 1, based on the first longitudinal folding line FL1 and the second longitudinal folding line FL2 in the longitudinal direction L. In the third folding step S4, it may be configured to fold back towards the rear surface side as shown in the drawings in the present embodiment or folded back towards a front side shown in the drawings. In the joining step S5, as shown in FIG. 12, an end of the packaging sheet 70 is pasted to a surface positioned at the outside of the packaging sheet 70 by means of the adhesive tape 75. Through this step, the absorbent article 1 is individually packaged in the packaging sheet 70.

By folding the absorbent article package as described above, a plane area of the absorbent article and the packaging sheet is reduced to one-ninth as compared to a case where they are spread, so that the absorbent article can be made compact.

Furthermore, other than a sanitary napkin, the absorbent article in the present invention may be a panty liner (vaginal discharge sheet), an incontinence pad, or the like.

Needless to say, the present invention includes various embodiments not described herein. Therefore, the technical range of the present invention is to be defined only by the inventive specific matter according to the adequate claims from the above description.

The entire contents of Japanese Patent Application Laid-open No. 2010-290079 (filed on Dec. 27, 2010) are incorporated in the present specification by reference.

INDUSTRIAL APPLICABILITY

In the absorbent article package, a first folding line based on which the absorbent article and the packaging sheet are folded towards the topsheet side; and a second folding line based on which the absorbent article and the packaging sheet are folded towards the backsheet side are formed in the longitudinal direction. Therefore, it is possible to provide the absorbent article package in which bending towards only one side (for example, the topsheet side) can be prevented by the action of the both folding lines. It is possible to the absorbent article package in which the absorbent article can be easily kept horizontal at the time of opening the absorbent article folded in a compact size, the absorbent article can be appropriately arranged along the inner surface of underwear, and the wearer can install the absorbent article on underwear.

REFERENCE SIGNS LIST 1, 2, 3, 4, 5, 600 . . . Absorbent article, 1A . . . Front end, 1B . . . Rear end, 10 . . . Topsheet, 20 . . . Backsheet, 21, 22 . . . Compressed unit, 30 . . . Absorber, 41, 42 . . . Sidesheet, 43, 44 . . . Wing unit, 45, 46 . . . End flap unit, 50 . . . Application region, 70 . . . Packaging sheet, 71 . . . Facing surface, 72 . . . Non-facing surface, 75 . . . Adhesive tape, 100, 101, 102, 103, 104, 105 . . . Absorbent article package

The invention claimed is:

1. An absorbent article package comprising:
   an absorbent article including an absorbent main body having a liquid-permeable topsheet, a liquid-impermeable backsheet and an absorber arranged between the topsheet and the backsheet; and
   a packaging sheet in which the absorbent article is individually packaged, wherein the absorbent article is individually packaged by folding the packaging sheet and the absorbent article in a state where the absorbent article is arranged on the packaging sheet;
   a folding line in a longitudinal direction of the absorbent article is formed in the packaging sheet and the absorbent article in a state where the individually-packaged absorbent article is opened; and
   the folding line includes:
   a first folding line based on which the absorbent article and the packaging sheet are folded towards the topsheet side; and
   a second folding line adjacent to the first folding line, based on which the absorbent article and the packaging sheet are folded towards the backsheet side,
   wherein:
   the absorbent article further includes wing units projecting from both ends in a widthwise direction of the absorbent main body towards an outside in the widthwise direction;
   a boundary between the first folding line and the second folding line is formed in the wing units in a region between both sides in the widthwise direction of each of the wing units as well as a region between both ends in the longitudinal direction of each of the wing units; and
   a length in the longitudinal direction of the second folding line is greater than a length in the longitudinal direction of the first folding line, in the region between the both sides in the widthwise direction of the wing units as well as the region between the both ends in the longitudinal direction of the wing units.

2. The absorbent article package according to claim 1, wherein
   the first folding line is formed at an outside in the longitudinal direction with respect to each of both ends in the longitudinal direction of the second folding line.

3. The absorbent article package according to claim 2, wherein
   the boundary is formed in the region between the both sides in the widthwise direction of the wing units as well as a region in the longitudinal direction between a maximum widthwise position having a greatest length in the widthwise direction of the wing units and the both ends in the longitudinal direction of the wing units.

4. The absorbent article package according to claim 1, wherein
   the first folding line is formed at an outside in the longitudinal direction with respect to each of both ends in the longitudinal direction of the second folding line in the region between the both sides in the widthwise direction of the wing units as well as the region between the both ends in the longitudinal direction of the wing units.

5. The absorbent article package according to claim 4, wherein
the boundary is formed in the region between the both sides in the widthwise direction of the wing units as well as a region in the longitudinal direction between a maximum widthwise position having a greatest length in the widthwise direction of the wing units and the both ends in the longitudinal direction of the wing units.

6. The absorbent article package according to claim 1, wherein
the boundary is formed in the region between the both sides in the widthwise direction of the wing units as well as a region in the longitudinal direction between a maximum widthwise position having a greatest length in the widthwise direction of the wing units and the both ends in the longitudinal direction of the wing units.

7. The absorbent article package according to claim 1, wherein:
the absorbent article further includes end flap units projecting from the both ends in the widthwise direction of the absorbent main body towards the outside in the widthwise direction, in a rear region of the absorbent article; and
a boundary between the first folding line and the second folding line is formed in a region between both sides in the widthwise direction of the end flap units as well as a region between both ends in the longitudinal direction of the end flap units.

8. A method of folding an absorbent article package having: an absorbent article including an absorbent main body having a liquid-permeable topsheet, a liquid-impermeable backsheet, and an absorber arranged between the topsheet and the backsheet; and a packaging sheet in which the absorbent article is individually packaged, the method comprising:
a first step of arranging the absorbent article on the packaging sheet;
a second step of folding a longitudinal end region of the absorbent article, including each of both ends in the longitudinal direction of the absorbent article, and the packaging sheet towards an inside based on a widthwise folding line along a widthwise direction perpendicular to the longitudinal direction; and
a third step of folding, after the first step and after the second step, a widthwise end region of the absorbent article including each of both ends in the widthwise direction of the absorbent article, and the packaging sheet towards the inside based on a longitudinal folding line along the longitudinal direction
wherein:
the absorbent article further includes wing units projecting from both ends in a widthwise direction of the absorbent main body towards an outside in the widthwise direction;
a boundary between the widthwise folding lines is formed in the wing units in a region between both sides in the widthwise direction of each of the wing units as well as a region between both ends in the longitudinal direction of each of the wing units; and
a length in the longitudinal direction of the second folding line is greater than a length in the longitudinal direction of the first folding line, in the region between the both sides in the widthwise direction of the wing units as well as the region between the both ends in the longitudinal direction of the wing units.

9. A method of folding an absorbent article package according to claim 8, wherein
the first folding line is formed at an outside in the longitudinal direction with respect to each of both ends in the longitudinal direction of the second folding line in the region between the both sides in the widthwise direction of the wing units as well as the region between the both ends in the longitudinal direction of the wing units.

10. A method of folding an absorbent article package according to claim 8, wherein
the boundary is formed in the region between the both sides in the widthwise direction of the wing units as well as a region in the longitudinal direction between a maximum widthwise position having a greatest length in the widthwise direction of the wing units and the both ends in the longitudinal direction of the wing units.

* * * * *